United States Patent [19]
Nies

[11] Patent Number: 6,160,033
[45] Date of Patent: Dec. 12, 2000

[54] PROCESS FOR PRODUCING BONE CEMENT CONTAINING ACTIVE SUBSTANCES

[75] Inventor: Berthold Nies, Fränkisch-Crumbach, Germany

[73] Assignee: Merck Patent Gesellschaft mit beschrankter Haftung, Darmstadt, Germany

[21] Appl. No.: 09/242,445

[22] PCT Filed: Aug. 13, 1997

[86] PCT No.: PCT/EP97/04434

§ 371 Date: Feb. 17, 1999

§ 102(e) Date: Feb. 17, 1999

[87] PCT Pub. No.: WO98/07456

PCT Pub. Date: Feb. 26, 1998

[30] Foreign Application Priority Data

Aug. 22, 1996 [DE] Germany .......................... 196 41 775

[51] Int. Cl.[7] .............................. A61K 6/087; A61F 2/28; C08L 33/12
[52] U.S. Cl. .......................... 523/116; 523/118; 524/533; 424/423
[58] Field of Search ..................................... 523/115, 116, 523/118; 524/533; 424/423

[56] References Cited

U.S. PATENT DOCUMENTS

| | | |
|---|---|---|
| 4,588,583 | 5/1986 | Pietsch et al. . |
| 4,722,948 | 2/1988 | Sanderson . |
| 5,650,108 | 7/1997 | Nies . |

FOREIGN PATENT DOCUMENTS

| | | |
|---|---|---|
| 2158402 | 3/1996 | Canada . |
| 0 164 483 | 12/1985 | European Pat. Off. . |

OTHER PUBLICATIONS

Buchholz et al, "Antibiotic loaded Acrylic Cement: Current Concepts," Clin. Orthopaedics and. Rel. Res., No. 190, pp. 96–108, Nov. 1984.

*Primary Examiner*—Peter A. Szekely
*Attorney, Agent, or Firm*—Millen, White, Zelano & Branigan, P.C.

[57] ABSTRACT

The invention relates to a process for the preparation of bone cements comprising active compound and to bone replacement materials or implantable drug depots produced therefrom. The bone cement is composed of a solid component and a liquid component. The liquid component is dissolved in an organic solvent whose proportion does not exceed 50% by weight based on the liquid component, and this solution is mixed with the solid component.

19 Claims, No Drawings

PROCESS FOR PRODUCING BONE CEMENT CONTAINING ACTIVE SUBSTANCES

The invention relates to a process for the preparation of bone cements comprising active compound and to bone replacement materials or implantable drug depots which can be produced therefrom.

Bone cements, bone replacement materials and implantable drug depots based on acrylate polymers have been known for a long time. Polymer materials based on acrylic and/or methacrylic esters have proved themselves here on the basis of their biocompatibility, their excellent strength properties, their favourable properties in respect of the release of incorporated pharmaceutical active compounds and, last but not least, on the basis of their utility-oriented processability.

Customary bone cements are composed of from about 50 to 75% by weight of a solid component which consists of a finely divided polymer of acrylic and/or methacrylic esters and, if desired, of further additives such as polymerization catalysts, X-ray contrast media, fillers and colorants, and of from about 25 to 50% by weight of a liquid component which consists of an acrylic and/or methacrylic ester monomer and, if desired, further additives such as polymerization accelerators and stabilizers. For use, the solid and the liquid component are combined to form a liquid to semisolid paste, which is optionally brought into a desired shape or is applied at the implantation site of a prosthesis to cement it in. The composition cures by means of the polymerization reaction that is induced with the mixing of the components.

A very common bone cement, for example, is one which, in a standard pack, comprises two bags of about 40 g of polymer powder each and two ampoules of 20 ml of monomer liquid each. The powder is a fine bead polymer of methyl methacrylate with a copolymer content of methyl acrylate. About 0.5% of dibenzoyl peroxide is added to the powder as a catalyst. During preparation the material is identified by copolymerizing small amounts of chlorophyll. The powder additionally comprises a customary X-ray contrast medium such as, for example, zirconium dioxide. The associated liquid consists of monomeric methyl methacrylate, to which about 0.7% of dimethyl-p-toluidine is added as a polymerization accelerator and small amounts of hydroquinone are added as a stabilizer. This liquid is also, in general, coloured with a small amount of chlorophyll for identification. The powder, packaged in polyethylene bags, is sterilized with ethylene oxide. The liquid is subjected to sterile filtration and dispensed into glass ampoules.

When 2 parts by weight of powder are mixed together with one part by weight of liquid, the dibenzoyl peroxide reacts with the dimethyl-p-toluidine in the liquid, which prompts the free-radical polymerization. The mixture is formulated such that it can be used as a doughy paste after only about one minute. This paste remains kneadable for a number of minutes and then begins to cure, giving off heat as it does so. After about 5 to 10 minutes the polymerization is essentially at an end. During the polymerization phase, for as long as the paste is still deformable, it can be brought into any desired shape, i.e. it can, for example, be introduced directly into the body for filling bone cavities or for cementing prostheses or can be used to produce shaped articles which cure outside the body and can then be used at any desired points of the body.

For numerous indications it is desirable for the bone cement to comprise pharmaceutical active compounds. Thus, bone cements comprising cytostatics can be employed for remedying bone defects following the removal of bone tumours. Bone cements which comprise antibiotics, antiseptics and, if desired, substances which promote bone growth are advantageous for cementing prostheses and for osteosynthesis. Shaped articles of bone cements comprising active compound can be implanted into soft tissue as local depots of active compound with delayed release of the active compound. Customary commercial bone cements with added antibiotics (e.g. Septopal®) are occasionally also used as active-compound vehicles for treating local infections. In addition, other antibiotics are added to such cements in order to increase the activity.

EP 0 202 445 A1, for example, describes such a bone cement comprising cytostatics, and also describes a drug depot produced therefrom which has particularly favourable release properties. This document reveals that the respective active compound is mixed in with the base material of the bone cement, i.e. with the prepolymer and/or with the monomer, as a finely divided powder, so that it is then present in homogeneous distribution within the corresponding polymer.

EP 0 701 824 A2 describes a process for producing bone cements comprising active compound, where the active compound is dissolved in an organic solvent and this solution is mixed with the liquid component or with the solid component. In this way, all three components of the bone cement can be provided in sterile form.

The addition of release promoters as powders to the cement is known per se. For example, DE 26 51 441 C2 describes the addition of amino acids.

The preformulated bone cement components, which are optimized primarily in respect of their mechanical properties or in respect of simplicity of sterilization of the components, however, do not meet the requirements that must be met by a medical product intended for implantation in the body, since they have only suboptimal properties for use as active-compound vehicles.

Manual mixing, such as the addition of release promoters as powders to the cement (e.g. salt, sugars, amino acids) as well, has the disadvantage that it is virtually impossible to achieve homogeneous and reproducible mixing. A nonhomogeneous mixture necessarily requires large additions of active compounds and auxiliaries in order to achieve the desired release. When customary commercial bone cements comprising active compound are used, the release remains usually well below the therapeutically desirable level. This is particularly true of implants having adverse geometric proportions (for example cement fillings).

The object was therefore to develop a process with which it is possible to provide, simply, bone cements and/or their precursor and successor products, comprising active compound, where the kinetics of the release of active compound are at the fore, i.e. where improved release of the active compound is achieved.

It has now been found that by mixing appropriate solvents in with the monomer component of bone cements the disadvantages described are avoided and it is possible to produce, from cements loaded with active compound, highly effective, implantable active-compound vehicles. A significantly higher release of active compound is achieved, the preparation of the bone cement is simple, and the amounts of active compound required are small.

The invention therefore provides a process for the preparation of a bone cement, bone replacement material or corresponding, implantable drug depot which comprises one or more active compounds and is based on acrylic and/or methacrylic ester polymers, by mixing a solid component (i) consisting essentially of polymeric acrylic and/or methacrylic ester in a proportion, relative to the bone cement, of from 50 to 75% by weight, and of one or more pharmaceutical active compounds with a liquid component (ii) consisting essentially of monomeric acrylic and/or methacrylic ester in a proportion of from 25 to 50% by weight, to form a liquid to semisolid, polymerizable paste, and, if desired, by shaping and curing thereof, characterized in that the liquid component (ii) is dissolved with an organic solvent whose proportion does not exceed 50% by weight based on (ii) and this solution is mixed with the solid component (i).

With the process according to the invention it is possible to use all customary bone cements based on acrylate/methacrylate and/or the starting materials customary for them. Bone cements of this kind are available commercially. Their composition and the manner of their preparation are familiar to the skilled worker.

To prepare a bone cement comprising active compound, it is envisaged according to the invention to dissolve the monomer component in an organic solvent and then to mix this monomer solution with the finely divided polymeric solid component of the bone cement, the latter component comprising the active compound. In preparing the cement mixture the solvent plays no part in the reaction, or participates as a polymerization partner, as in the case of vinylpyrrolidone. The monomer solution is subjected to sterile filtration beforehand, while the solid component is subjected to a final sterilization by means of radiation and/or ethylene oxide.

Solvents suitable for preparing the monomer solution are essentially all customary organic solvents. Examples of preferred solvents are 2-pyrrolidone, N-methylpyrrolidone, dimethyl sulfoxide (DMSO), tetrahydrofuran (THF), dioxane, ethylene glycol, propanediol, vinylpyrrolidone or mixtures of these solvents. It is judicious to select those solvents in which the intended monomer dissolves well. The amount of solvent is chosen so as not to exceed 50% by weight, based on the liquid monomer. This ensures that, when mixing the components to form the ready-to-use bone cement, the processing properties, curing characteristics and mechanical strength of the cured bone cement do not alter too greatly. The amount of solvent chosen is preferably such that its proportion is from 1 to 25% by weight, in particular from 5 to 20% by weight, based on the liquid monomer component.

The amount of pharmaceutical active compound employed which is mixed in with the bone cement is dependent on its specific activity, on the medical indication and on the particular set of requirements to which the bone cement or the bone replacement material or the drug depot to be prepared from it is subject. Generally speaking, a proportion of pharmaceutical active compound of from 0.1 to 5% by weight, based on the overall amount of bone cement, is sufficient; in some individual cases, especially when preparing implantable drug depots, however, the proportion of active compound may be even higher, for instance up to 40% by weight.

Suitable active compounds are preferably cytostatics such as methotrexate, cisplatin, cyclophosphamide, fluorouracil, doxorubicin, etc., antibiotics such as vancomycin, netilmicin, gentamicin, clindamycin, vancomycin, teicoplanin, etc., and also antiseptics, and bone growth promoters.

It has surprisingly been found that the release properties of bone cement comprising, say, antibiotics, which has been prepared by the process according to the invention, are considerably better than if the monomer component is mixed directly in with the solid component, as has been the case to date.

Of course, the release properties of the active compound can also be influenced and, if appropriate, improved further by means of the known and customary additives. Suitable additives of this kind are amino acids, such as arginine, and also hydroxyapatile or sodium bicarbonate, as far as possible in finely divided form with particle sizes below 100 $\mu$m. By means of additives of this kind it is possible, in particular, to regulate the initial concentration of the release of active compound.

The solid component, which is usually in the form of a bead polymer of methyl methacrylate-methyl acrylate copolymer with particle sizes of between 5 and 250 $\mu$m, comprises a polymerization catalyst, such as dibenzoyl peroxide, and the pharmaceutical active compound. It may also comprise X-ray contrast media, such as zirconium dioxide, for example, dyes for identification, such as chlorophyll, and also fillers and, if desired, further additives. Examples of common fillers are osteoinductive or osteoconductive calcium phosphates, such as, in particular, hydroxyapatile and tricalcium phosphate. The proportion of all these additives can vary widely and is dependent on the respective set of requirements to which the bone cement and/or the corresponding successor products are subject. In general it barely exceeds 30% by weight, based on the solid component. The liquid monomer component, methyl methacrylate, generally comprises a polymerization accelerator, such as dimethyl-p-toluidine, and hydroquinone as stabilizer, in the amounts customary for these additives. It is also possible for dyes and any other judicious additives to be present. The solid component can be sterilized readily with $\gamma$ radiation or with ethylene oxide; the liquid component can be subjected to sterile filtration. Both components can be dispensed separately and under sterile conditions into appropriate containers.

The bone cement containing active compound is judiciously provided in the form of a kit composed of separate packs of the two principal components. Component (a) comprises the solid component, consisting of a finely divided polymer of acrylic and/or methacrylic esters, a pharmaceutical active compound and, if desired, further additives, such as polymerization catalysts, X-ray contrast media, fillers and dyes, whose proportion is from about 50 to 75% by weight of the bone cement. Component (b) comprises the liquid component, consisting of an acrylic and/or methacrylic acid monomer and, if desired, further additives such as polymerization accelerators, stabilizers and release promoters, whose proportion is from about 25 to 50% by weight of the bone cement, in an organic solvent whose proportion does not exceed 50% by weight based on the liquid component.

The amounts of the components are preferably tailored to one another in such a way that the entire contents of the two packs are combined with one another. The tailoring of amounts is performed in accordance with the intended utility and depends on whether a cement of low, medium or high viscosity is required. The solid component in this case has been subjected to a final sterilization by means of radiation or ethylene oxide, the liquid monomer solution has been subjected to sterile filtration, and both components are dispensed under sterile conditions into appropriate packaging.

It is judicious to supplement this kit with a device for mixing and/or applying the bone cement. Appropriate devices are known and common. Preferably, appropriate devices enable the bone cement to be mixed under vacuum and make it possible for the cement to be applied in combination using a bone cement syringe.

The preparation of the ready-to-use bone cement comprising active compound and its further processing are carried out in full analogy with prior art bone cement systems. The bone cement comprising active compound can be used in a customary manner during the liquid or plastic stage for the implantation of bone prostheses. The surgeon is also able to process the composition to give shaped articles of any shape and size, and, after curing, to implant them as local depots of active compound into the areas of the body that are to be treated. Implantable drug depots of this kind can also be offered in prefabricated form.

EXAMPLE 1

A bone cement comprising 2 g of vancomycin as powder in 40 g of Osteopal® cement powder (consisting of polymethyl methacrylate, chlorophyll, benzoyl peroxide and zirconium dioxide) is stirred with 20 ml of methyl methacrylate monomer. 3 further samples are prepared correspondingly with methyl methacrylate monomer to which 0.2, 1.0 and 4 ml, respectively, (1, 5 and 20% by weight, respectively,) of propanediol have been added. The runny cement paste is introduced into a two-part metal mould having spherical cavities with a diameter of 7 mm. After the cement has cured, the spheres are removed and the release of the active compound is determined in vitro by a standardized method.

Table 1 shows the daily release of vancomycin in μg/ml from the respective bone cement spheres. This increases on addition of 1 ml (5% by weight) of propanediol to the monomer by a factor of 5 at its peak (day 1). Even at later points in time, the release remains from about 3 to 5 times as great as with the initial cement.

TABLE 1

Release of vancomycin [μg/ml]

| Day | 0% by weight propanediol | 1% by weight propanediol | 5% by weight propanediol | 20% by weight propanediol |
| --- | --- | --- | --- | --- |
| 0.1 | 25.88 | 34.69 | 74.70 | 70.20 |
| 1 | 47.06 | 74.17 | 233.61 | 238.63 |
| 2 | 25.75 | 35.45 | 86.03 | 129.44 |
| 3 | 18.49 | 24.84 | 59.11 | 100.47 |
| 4 | 14.49 | 26.30 | 51.24 | 86.21 |
| 5 | 14.87 | 29.68 | 47.00 | 79.06 |
| 6 | 17.33 | 28.25 | 57.27 | 80.59 |
| 7 | 11.78 | 21.53 | 48.86 | 56.06 |
| 8 | 9.78 | 20.50 | 37.78 | 47.01 |
| 9 | 10.41 | 17.30 | 23.89 | 41.64 |
| 10 | 8.86 | 12.97 | 23.76 | 33.54 |
| 14 | 5.19 | 9.71 | 15.13 | 23.89 |
| 28 | 2.26 | 3.36 | 5.46 | 21.42 |
| 84 | 0.79 | 1.09 | 2.78 | 4.31 |

EXAMPLE 2

A bone cement comprising 2 g of netilmicin as powder in 40 g of Osteopal cement powder is stirred together with 20 ml of methyl methacrylate monomer. 3 further samples are prepared correspondingly with methyl methacrylate monomer to which 0.2, 1.0 and 4 ml, respectively, (1, 5 and 20% by weight, respectively,) of propanediol have been added. The runny cement paste is introduced into a two-part metal mould having spherical cavities with a diameter of 7 mm. After the cement has cured, the spheres are removed and the release of the active compound is determined in vitro in accordance with a standardized method.

Table 2 shows the daily release of netilmicin in μg/ml from the respective bone cement spheres. The release of netilmicin is relatively high at its peak even in the initial cement, but then falls off rapidly. The addition of 1 ml of propanediol (5% by weight) doubles the peak value (day 1). Over the subsequent days, up to day 9, the difference becomes larger up to a factor of about 10 and then remains virtually constant.

TABLE 2

Release of netilmicin [μg/ml]

| Day | 0% by weight propanediol | 1% by weight propanediol | 5% by weight propanediol | 20% by weight propanediol |
| --- | --- | --- | --- | --- |
| 0.1 | 100.99 | 285.95 | 282.95 | 308.77 |
| 1 | 335.62 | 498.29 | 634.96 | 783.22 |
| 2 | 52.05 | 60.06 | 142.97 | 248.30 |
| 3 | 34.96 | 32.55 | 82.82 | 170.64 |
| 4 | 23.16 | 21.00 | 96.48 | 150.83 |
| 5 | 29.16 | 22.62 | 64.50 | 125.63 |
| 6 | 15.83 | 26.94 | 121.44 | 113.52 |
| 7 | 17.64 | 10.53 | 125.40 | 114.85 |
| 8 | 9.45 | 5.06 | 88.14 | 92.98 |
| 9 | 5.53 | 4.59 | 58.96 | 50.36 |
| 10 | 4.45 | 3.30 | 50.91 | 42.47 |
| 14 | 3.24 | 1.74 | 35.09 | 23.04 |
| 28 | 1.69 | 1.05 | 15.97 | 5.42 |
| 84 | 0.43 | 0.23 | 3.76 | 1.14 |
| 168 | 0.22 | 0.20 | 2.36 | 0.47 |

What is claimed is:

1. Process for the preparation of a bone cement, bone replacement material or corresponding, implantable drug depot which comprises one or more active compounds and is based on acrylic and/or methacrylic ester polymers, said process comprising mixing a solid component (i) consisting essentially of polymeric acrylic and/or methacrylic ester in a proportion, relative to the bone cement, of from 50 to 75% by weight, and of one or more pharmaceutical active compounds with a liquid component (ii) consisting essentially of monomeric acrylic and /or methacrylic ester in a proportion, relative to the bone cement, of from 25 to 50% by weight, to form a liquid to semisolid, polymerizable paste, and, optionally, the shaping and curing thereof, wherein the liquid component (ii) is dissolved with an organic solvent whose proportion is from 1 to 25% by weight based on (ii) and the resultant solution is mixed with the solid component (i), and wherein said solvent is 2-pyrrolidone, N-methylpyrrolidone, vinylpyrrolidone, dimethyl sulfoxide, tetrahydrofuran, dioxane, propanediol or combinations thereof.

2. Process according to claim 1, wherein the proportion of solvent is from 5 to 20% by weight, based on the liquid component.

3. Process according to claim 1, wherein the solid component is subjected to a final sterilization by means of radiation, ethylene oxide, or both, and the liquid component is subjected to sterile filtration.

4. Kit for the preparation of bone cement which promotes the release of active compound, said kit comprising separate packs of (a) a solid component whose proportion is from about 50 to 75% by weight of the bone cement, consisting essentially of a finely divided polymer of acrylic and/or methacrylic esters and of a pharmaceutical active compound, and (b) a solution of a liquid component, whose proportion is from about 25 to 50% by weight of the bone cement, consisting essentially of an acrylic and/or methacrylic acid monomer in an organic solvent whose proportion of solvent is from 1 to 25% by weight based on the liquid component, and wherein said solvent is 2-pyrrolidone, N-methylpyrrolidone, vinylpyrrolidone, dimethyl sulfoxide, tetrahydrofuran, dioxane, propanediol or combinations thereof.

5. Kit according to claim 4, further comprising a device for mixing the bone cement.

6. Kit according to claim 4, wherein the pack unit (a) has been subjected to a final sterilization by means of radiation, ethylene oxide, or both, and the contents of the pack unit (b) have been subjected to sterile filtration.

7. Kit according to claim 4, further comprising a device for applying the bone cement.

8. Kit according to claim 5, further comprising a device for applying the bone cement.

9. The process according to claim 1, wherein the pharmaceutical active compound is a cytostatic agent.

10. The process according to claim 9, wherein the cytostatic agent is methotrexate, cisplatin, cyclophosphamide, fluoracil, or doxorubicin.

11. The process according to claim 1, wherein the pharmaceutical agent is an antibiotic.

12. The process according to claim 11, wherein the antibiotic is vancomycin, netilmicin, gentamicin, clindamycin, vancomycin, or teicoplanin.

13. The process according to claim 1, wherein the polymer is polymethyl methacrylate.

14. The process according to claim 1, wherein the pharmaceutical active agent is an antiseptic.

15. The process according to claim 1, wherein the pharmaceutical active agent is a bone growth promoter.

16. The process according to claim 1, further comprising amino acids, hydroxyapatile, sodium bicarbonate, x-ray contrast media, or dye.

17. The process according to claim 15, wherein the x-ray contrast media is zirconium dioxide.

18. The process according to claim 1, wherein the proportion of pharmaceutical active compound is from 0.1 to 5% by weight, based on the bone cement.

19. The process according to claim 1, wherein the monomer is methyl methacrylate.

* * * * *

UNITED STATES PATENT AND TRADEMARK OFFICE
CERTIFICATE OF CORRECTION

PATENT NO. : 6,160,033
DATED : December 12, 2000
INVENTOR(S) : Berthold Nies

It is certified that error appears in the above-identified patent and that said Letters Patent is hereby corrected as shown below:

Column 8,
Line 15, reads "hydroxyapatile" should read -- hydroxylapatite --

Signed and Sealed this

Third Day of May, 2005

JON W. DUDAS
*Director of the United States Patent and Trademark Office*